United States Patent [19]

Hoefle et al.

[11] Patent Number: 4,743,605

[45] Date of Patent: May 10, 1988

[54] SATURATED FATTY ACID AMIDES AS INHIBITORS OF ACYL-COA:CHOLESTEROL ACYLTRANSFERASE

[75] Inventors: Milton L. Hoefle, Ann Arbor; Ann Holmes, Dexter; Bruce D. Roth, Ann Arbor, both of Mich.

[73] Assignee: Warner-Lambert Company, Morris Plains, N.J.

[21] Appl. No.: 103,316

[22] Filed: Oct. 1, 1987

Related U.S. Application Data

[62] Division of Ser. No. 017,960, Feb. 24, 1987, Pat. No. 4,716,175.

[51] Int. Cl.[4] .................. A61K 31/505; C07D 239/46; C07D 239/34; C07D 239/28
[52] U.S. Cl. .................................... 514/269; 544/319; 544/301; 544/311
[58] Field of Search ....................... 544/319, 301, 311; 514/269

[56] References Cited

U.S. PATENT DOCUMENTS 4,250,178  2/1981  Bucher et al. ...................... 544/319
4,410,697  10/1983  Torok et al. ...................... 544/165

OTHER PUBLICATIONS

Chem. Abstracts, vol. 76, No. 3, 14463j.
Chem. Abstracts, Volkenshtein et al., vol. 104, 199590m, (1986).
Chem. Abstracts, Boyes et al., vol. 94, 121134w, (1981).

Primary Examiner—Alan L. Rotman
Assistant Examiner—J. Richter
Attorney, Agent, or Firm—Jerry F. Janssen

[57] ABSTRACT

Certain substituted amides of saturated fatty acids are potent inhibitors of the enzyme acyl-CoA:cholesterol acyltransferase and are thus useful agents for inhibiting the intestinal absorption of cholesterol.

4 Claims, No Drawings

SATURATED FATTY ACID AMIDES AS INHIBITORS OF ACYL-CoA:CHOLESTEROL ACYLTRANSFERASE

CROSS REFERENCE TO RELATED APPLICATIONS

This application is a divisional of application Ser. No. 017,960 filed Feb. 24, 1987, now U.S. Pat. No. 4,716,175.

BACKGROUND OF THE INVENTION

This invention relates to chemical compounds having pharmacological activity, to pharmaceutical compositions which include these compounds, and to a pharmaceutical method of treatment. More particularly, this invention concerns certain substituted amides of α-substituted or α,α-disubstituted alkanoic and alkenoic acids which inhibit acyl-coenzyme A: cholesterol acyltransferase (ACAT), pharmaceutical compositions containing these compounds, and a method of inhibiting intestinal absorption of cholesterol.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, it is now known that cholesterol is carried to the sites of deposit in blood vessels in the form of low density lipoprotein cholesterol (LDL cholesterol) and away from such sites of deposit in the form of high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the absorption of dietary cholesterol into the body through the intestinal wall.

In intestinal mucosal cells dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides a class of compounds with ACAT inhibitory activity having the structure

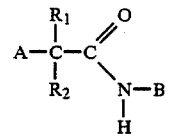

where A is an unbranched hydrocarbon group containing from one to twenty carbon atoms and which may contain from one to three carbon-carbon double bonds.

$R_1$ is hydrogen or alkyl of from one to four carbon atoms or phenylmethyl and $R_2$ is alkyl of from one to four carbon atoms or phenylmethyl. Alternatively, $R_1$ and $R_2$, taken together with the carbon atom to which they are attached may form a saturated carbocyclic ring of from three to seven carbon atoms.

B is selected from

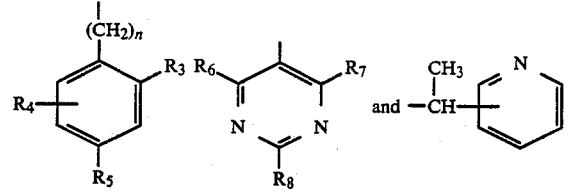

where n is zero or one, $R_3$, $R_4$, and $R_5$ are independently selected from hydrogen, fluorine, chlorine, bromine, trifluoromethyl, alkyl of from one to four carbon atoms, and alkoxy of from one to four carbon atoms.

$R_6$ is alkoxy of from one to four carbon atoms, and $R_7$ and $R_8$ are independently hydrogen or alkoxy of from one to four carbon atoms.

The terms "alkyl" as used throughout this specification and the appended claims means a branched or unbranched hydrocarbon grouping derived from a saturated hydrocarbon by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

The term "alkoxy" means an alkyl group, as defined above, attached to the parent molecular moiety through an oxygen atom.

The term "halogen" contemplates fluorine, chlorine, or bromine.

Those compounds of the present invention in which the α-carbon atom of the acid portion of the amide is only monosubstituted possess an asymmetric center at that carbon atom and are capable of existing in two enantiomeric forms. Likewise, an asymmetric center exists at $C_1$ of the ethyl group in those compounds of this invention where the "B" substituent is 1-(2-, 3-, or 4-pyridinyl)ethyl. The present invention contemplates all possible optical isomeric forms as well as mixtures thereof.

DETAILED DESCRIPTION

The compounds of the present invention provide a class of amides of α-substituted or α,α-disubstituted straight-chain acids which are inhibitors of the enzyme acyl-CoA: cholesterol acyltransferase (ACAT) and are thus useful as pharmacological agents for inhibiting the intestinal absorption of cholesterol.

The compounds of the present invention are substituted with phenylmethyl groups or one or more alkyl groups, containing from one to four carbon atoms, on the α-carbon atom of the acid portion of the amide. Preferred compounds of the invention are those in which the α-carbon substituents, $R_1$ and $R_2$ are methyl, ethyl or phenylmethyl or those compounds where $R_1$ and $R_2$ taken together with the carbon atom to which they are attached form a saturated carbocyclic ring of from three to seven carbon atoms. It has been found, in accordance with the present invention, that when one or more alkyl groups are attached to the α-carbon (i.e. the carbon atom immediately adjacent to the carbonyl function) of the acid residue of the amide compounds of this invention, the in vivo ACAT inhibitory activity of the compounds is enhanced over the corresponding unsubstituted compounds.

The amide nitrogen of the compounds of this invention is substituted with a group selected from phenyl or benzyl, either of which may be mono-, di-, or trisubstituted with fluorine, chlorine, bromine, trifluoromethyl, alkyl, or alkoxy; mono-, di, or trisubstituted pyrimidin-5-yl; or 1-(2-, 3- or 4-pyridinyl)ethyl.

Preferred compounds of the present invention are those in which the alkyl or alkoxy substituents contain one or two carbon atoms, i.e. methyl, ethyl, methoxy, and ethoxy.

Compounds falling within the scope of the present invention are exemplified by the following:

N-(2,6-Dimethylphenyl)-2,2-dimethyldodecanamide.
N-(2,6-Diethylphenyl)-2,2-dimethyldodecanamide.
N-[2,6-bis(1-Methylethyl)phenyl]-2,2-dimethyldodecanamide.
N-(2-Ethoxy-6-methylphenyl)-2,2-dimethyldodecanamide.
2-Methyl-N-[2,6-bis(1-methylethyl)phenyl]tetradecanamide.
(Z)-N-(2,6-Diethylphenyl-2-methyl-9-octadecenamide.
(Z)-N-(2,6-Diethylphenyl)-2,2-dimethyl-9-octadecenamide.
(Z)-N-(2-Methoxy-6-methylphenyl)-2,2-dimethyl-11-eicosenamide.
2,2-Dimethyl-N-(2,4,6-trimethoxyphenyl)dodecanamide.
2-Methyl-N-(2,4,6-trimethoxyphenyl)tetradecanamide.
2-Ethyl-N-(2,4,6-trimethoxyphenyl)tetradecanamide.
2,2-Dimethyl-N-(2,4,6-trimethoxyphenyl)tetradecanamide.
2-Methyl-N-(2,4,6-trimethoxyphenyl)hexadecanamide.
2,2-Dimethyl-N-(2,4,6-trimethoxyphenyl)hexadecanamide.
2,2-Dimethyl-N-(2,4,6-trimethoxyphenyl)octadecanamide.
1-Decyl-N-(2,4,6-trimethoxyphenyl)cyclobutanecarboxamide.
1-Decyl-N-(2,4,6-trimethoxyphenyl)cyclopentanecarboxamide.
(Z)-2-Methyl-N-(2,4,6-trimethoxyphenyl)-9-octadecenamide.
(Z)-2,2-Dimethyl-N-(2,4,6-trimethoxyphenyl)-9-octadecenamide.
(Z)-2,2-Dimethyl-N-(2,4,6-trimethoxyphenyl)-11-eicosenamide.
N-(4,6-Dimethoxy-5-pyrimidinyl)-2,2-dimethyldodecanamide.
N-(4,6-Dimethoxy-2-phenyl-5-pyrimidinyl)-2,2-dimethyldodecanamide.
N-(4,6-Dimethoxy-5-pyrimidinyl)-2-methyltetradecanamide.
N-(4,6-Dimethoxy-5-pyrimidinyl)-2-ethyltetradecanamide.
N-(4,6-Dimethoxy-5-pyrimidinyl)-2,2-dimethyltetradecanamide.
N-(4,6-Diethoxy-5-pyrimidinyl)-2-methyltetradecanamide.
1-Decyl-N-(4,6-dimethoxypyrimidin-5-yl)cyclopentanecarboxamide.
(Z)-N-(4,6-Dimethoxy-5-pyrimidinyl)-2,2-dimethyl-11-eicosenamide.
2-Methyl-N-[1-(2-pyridinyl)ethyl]dodecanamide.
2-Ethyl-N-[1-(2-pyridinyl)ethyl]dodecanamide.
2-Propyl-N-[1-(2-pyridinyl)ethyl]dodecanamide.
α-Decyl-N-[1-(2-pyridinyl)ethyl]benzenepropanamide.
2-Methyl-N-[1-(2-pyridinyl)ethyl]tetradecanamide.
2-Ethyl-N-[1-(2-pyridinyl)ethyl]tetradecanamide.
2-Methyl-N-[1-(2-pyridinyl)ethyl]hexadecanamide.
2,2-Dimethyl-N-[1-(2-pyridinyl)ethyl]hexadecanamide.

The compounds of the present invention are prepared by reacting the acid chloride of the appropriate α-substituted or α,α-disubstituted acid with the desired substituted amine in a polar solvent such as tetrahydrofuran, chloroform, dimethylformamide, and the like in the presence of a tertiary amine acid scavenger such as triethylamine.

The reaction may be carried out at any temperature between 0° C. and the boiling point of the solvent, with lower temperatures being preferred.

The reaction is allowed to proceed until analysis of the mixture by a means such as chromatography indicates substantially complete reaction between the acid chloride and the substituted amine. Reaction times may vary between about two hours to about 24 hours, depending upon the particular reagents and reaction temperature employed.

Starting materials are known or, if not previously known, are prepared by methods well known in the art. For example, the starting α-alkyl-substituted acids are prepared by first converting diethyl malonate to the desired alkyl diethyl malonate and then reacting the sodio-salt of the alkyl diethyl malonate with a bromoalkane using conventional methods. The product of this reaction is then hydrolyzed and decarboxylated by well known methods to produce the α-(alkyl-substituted) acid. The acid is converted to the acid chloride by reaction with thionyl chloride, oxalyl chloride, phosphoryl chloride or the like by conventional methods.

The starting α,α-dialykl-substituted acids may be prepared by either of two alternative methods. In the case where both α-substituents are methyl, the appropriate bromoalkane is reacted with the lithio salt of iso-butyric acid or an ester of isobutyric acid to produce the desired α,α-dimethyl acid.

In the alternative method for preparing the α,α-dialkyl-substituted acids, the appropriate bromoalkane is reacted with the sodio salt of diethyl malonate, to produce the alkyl-substituted diethyl malonate. This ester is then hydrolyzed to the corresponding alkyl-substituted malonic acid and decarboxylated in the conventional manner. The resulting monocarboxylic acid is then α-alkylated by first converting the acid to its α-lithio carbanion salt, and then reacting that salt with the appropriate alkyl halide. A second α-alkyl substituent is attached by repeating this procedure.

Details for the reaction conditions for preparing the α-lithio carbanion salt of acids or esters, and for the conversion of these salts to α-alkyl-substituted acids or esters is found in P. Creger, Org. Syn., Vol. 50, pp 58 ff., John Wiley & Sons, New York, 1970.

The substituted benzeneamine and substituted phenylmethylamine starting materials are prepared by methods well known in the art.

The substituted pyrimidin-5-ylamines are prepared from the mono-, di-, or trichloropyrimidines by first nitrating the chloropyrimidines to produce the chlorinated 5-nitropyrimidines. The chlorine substituents are then replaced by alkoxy substituents by heating the nitrochloropyrimidines with the sodium salt of the desired alcohol in the same alcohol as solvent under reflux conditions. Following conversion of the chloro-5-nitropyrimidines to the corresponding alkoxy-5-nitropyrimidines, the nitro group is reduced to an amine function in the conventional manner as, for example, by catalytic hydrogenation.

As shown by the data presented below in Table 1 the compounds of the present invention are potent inhibitors of the enzyme acyl-CoA: cholesterol acyltransferase (ACAT), and are thus effective in inhibiting the esterification and transport of cholesterol across the intestinal cell wall.

The ability of representative compounds of the present invention to inhibit ACAT was measured using an in vitro test more fully described in Field, F. J. and Salone, R. G., Biochemica et Biophysica 712: 557–570 (1982). The test assesses the ability of a compound to inhibit the acylation of cholesterol by oleic acid by measuring the amount of radio-labeled cholesterol oleate formed from radio-labeled oleic acid in a tissue preparation containing rabbit intestinal microsomes.

The data appear in Table 1 where they are expressed as $IC_{50}$ values; i.e. the concentration of test compound required to inhibit cholesterol esterification by 50%.

TABLE 1

| Compound | $IC_{50}$ (Micromolar) |
| --- | --- |
| N—(2,6-dimethylphenyl)-2,2-dimethyldodecanamide | 1.3 |
| N—(2-ethoxy-6-methylphenyl)-2,2-dimethyldodecanamide | 0.23 |
| (Z)—N—(2-methoxy-6-methylphenyl)-2,2-dimethyl-11-eicosenamide | 0.68 |
| 2,2-dimethyl-N—(2,4,6-trimethoxyphenyl)dodecanamide | 0.042 |
| 2-methyl-N—(2,4,6-trimethoxyphenyl)tetradecanamide | 0.13 |
| 2-ethyl-N—(2,4,6-trimethoxyphenyl)tetradecanamide | 0.05 |
| 2,2-dimethyl-N—(2,4,6-trimethoxyphenyl)tetradecanamide | 0.063 |
| 2-methyl-N—(2,4,6-trimethoxyphenyl)hexadecanamide | 0.031 |
| 2,2-dimethyl-N—(2,4,6-trimethoxyphenyl)hexadecanamide | 0.044 |
| 2,2-dimethyl-N—(2,4,6-trimethoxyphenyl)octadecanamide | 0.087 |
| 1-decyl-N—(2,4,6-trimethoxyphenyl)cyclopentanecarboxamide | 0.007 |
| (Z)—2-methyl-N—(2,4,6-trimethoxyphenyl)-9-octadecenamide | 0.034 |
| (Z)—2,2-dimethyl-N—(2,4,6-trimethoxyphenyl)-9-octadecenamide | 0.044 |
| (Z)—2,2-dimethyl-N—(2,4,6-trimethoxyphenyl)-11-eicosenamide | 0.11 |
| N—(4,6-dimethoxy-5-pyrimidinyl)-2,2-dimethyldodecanamide | 0.23 |
| N—(4,6-dimethoxy-5-pyrimidinyl)-2-methyltetradecanamide | 0.40 |
| N—(4,6-dimethoxy-5-pyrimidinyl)-2-ethyltetradecanamide | 0.26 |
| N—(4,6-dimethoxy-5-pyrimidinyl)-2,2-dimethyltetradecanamide | 1.3 |

TABLE 1-continued

| Compound | $IC_{50}$ (Micromolar) |
| --- | --- |
| N—(4,6-dimethoxy-5-pyrimidinyl)-2-methyltetradecanamide | 0.5 |
| (Z)—N—(4,6-dimethoxy-5-pyrimidinyl)-2,2-dimethyl-11-eicosenamide | 0.78 |
| 2-methyl-N—[1-(2-pyridinyl)ethyl]-dodecanamde | 3.3 |
| 2-ethyl-N—[1-(2-pyridinyl)ethyl]-dodecanamide | 1.6 |
| 2-propyl-N—[1-(2-pyridinyl)ethyl]-dodecanamrde | 3.7 |
| α-decyl-N—[1-(2-pyridinyl)ethyl]-benzenepropanamide | 7.0 |
| 2-methyl-N—[1-(2-pyridinyl)ethyl]-tetradecanamide | 0.8 |
| 2-ethyl-N—[1-(2-pyridinyl)ethyl]-tetradecanamide | 0.7 |
| 2-methyl-N—[1-(2-pyridinyl)ethyl]-hexadecanamide | 1.4 |
| 2,2-dimethyl-N—[1-(2-pyridinyl)ethyl]-hexadecanamide | 0.7 |

In Vivo Tests

In the cholesterol-fed rabbit test, male, New Zealand white rabbits weighing approximately 1 kg were fed a normal diet 40 g per day of rabbit chow (Purina No. 5321, Ralston Purina Co., 711 West Fuesser Road, Mascoutah, Ill., 62224, USA). After six days on this diet, the rabbits were fed 50 g per day for three days of a cholsterol-enriched diet consisting of one part of a cholesterol-containing chow (Purina Catalog No. 841206WLI, 0.25% cholesterol) and two parts of normal chow. Next, the rabbits were fed 60 g per day for four days of a cholsterol-enriched diet consisting of two parts of a cholesterol-containing chow (Purina Catalog No. 841206WLI, 0.25% cholesterol) and one part of normal chow.

After this meal adaptation and cholesterol loading period, the test compounds of this invention were administered to the test animals in oral doses of 50 mg/kg of body weight thirty minutes prior to each meal for seven days. Control animals were administered vehicle only.

The animals were sacrificed three hours after their last meal in the postabsorptive state. Serum cholesterol levels were determined for each animal, and the data appear in Table 2 expressed as percent change in serum cholesterol level compared to control.

In the cholesterol-fed rat test, male, Sprague-Dawley rats (approximately 200 g body weight) were randomly divided into groups and provided ad libitum a regular rat chow diet (Purina No. 5002) supplemented with 5.5% peanut oil, 1.5% cholesterol and 0.3% cholic acid, with or without drug admixed at the indicated levels (w/w). After one week, the animals (nonfasted) were etherized and blood was taken from the heart into EDTA (0.14% final concentration) to measure total cholesterol using the Abbott VP Analyzer.

The results of in vivo testing of representative compounds of the present invention are presented in Table 2.

TABLE 2

| Compound | Percent Reduction in Cholesterol | |
| --- | --- | --- |
| | Rabbit | Rat |
| 2,2-Dimethyl-N—(2,4,6-trimethoxyphenyl)dodecanamide | −67 | −54 |

TABLE 2-continued

| Compound | Percent Reduction in Cholesterol | |
|---|---|---|
| | Rabbit | Rat |
| 2-methyl-N—(2,4,6-trimethoxyphenyl)tetradecanamide | −45 | −52 |
| N—(4,6-dimethoxy-5-pyrimidinyl)-2-methyltetradecanamide | −29 | −29 |
| 1-Decyl-N—(2,4,6-trimethoxy phenyl)cyclopentanecarboxamide | | −52 |
| N—(4,6-dimethoxy-5-pyrimidinyl)-2-methyltetradecanamide | | −34 |

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium, carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as agents for the inhibition of intestinal absorption of cholesterol, the compounds utilized in the pharmaceutical method of this invention are administered to the patient at dosage levels of from 500 to 2000 mg per day. For a normal human adult of approximately 70 kg of body weight, this translates into a dosage of from 7 to 30 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention, and are illustrative thereof. They are not to be read as limiting the scope of the invention as it is defined by the appended claims.

Representative Example of the Preparation of an α,α-Dialkylalkanoic Acid

Preparation of 2,2-Dimethyloctadecanoic Acid

Diisopropyl amine (20.6 ml, 28.6 g, 0.283 mol) was dissolved in 250 ml of dry tetrahydrofuran. To this mixture was added 13.6 g (0.283 mol) of 50% sodium hydride. Isobutyric acid (26.2 ml, 24.9 g, 0.283 mol) was added dropwise with stirring and the temperature was allowed to rise. After addition of the acid was complete, the mixture was heated under reflux for an additional 20 minutes. The mixture was then cooled to 0° C. and 118 ml (0.283 mol) of 2.4M n-butyllithium was slowly added while maintaining the temperature below 5° C. When addition was complete, the mixture was stirred at ice-bath temperature for 15 minutes and then allowed to warm to room temperature and stirred for an additional two hours.

The mixture was cooled to 0° C. and 99.7 g (0.283 mol) of 1-iodohexadecane were added dropwise. The resulting mixture was stirred at ice bath temperature for one hour, allowed to warm to room temperature and stirred at room temperature overnight.

The mixture was again cooled to 0° C. and 400 ml of water was added with cooling. The aqueous layer was extracted with diethyl ether and the combined organic layers were dried and evaporated to yield a heavy gum. This material was taken up in hot water, the solution was made strongly acid with concentrated hydrochloric acid. This mixture was extracted with diethyl ether, the ether layer separated, washed with brine, dried, and evaporated to yield 92.1 g of 2,2-dimethyloctadecanoic acid, mp 50°-53° C.

Representative Example of the Preparation of an α-Alkylalkanoic Acid (Alternative Method)

Preparation of 2-Methylhexadecanoic Acid

Sodium metal (12.06 g, 0.52 mol) was dissolved in 400 ml of absolute ethanol. 2-Methyl-1,3-propanedioic acid, diethyl ester (95.8 g (0.55 mol) was added dropwise to the sodium ethoxide solution with stirring. When the addition was complete, the mixture was heated under reflux for 15 minutes.

1-Bromotetradecane (138.65 g, 0.5 mol) was added dropwise with stirring the the above mixture, and the resulting mixture was stirred and heated under reflux overnight.

After this time, the mixture was cooled, neutralized with acetic acid, and concentrated under vacuum to half its original volume. This residue was diluted with water and the aqueous phase was separated and extracted twice with diethyl ether. The organic layers were combined, washed with water, dried over anhydrous magnesium sulfate, and evaporated to yield an oil.

This oil was mixed with 112 g (1.7 mol) of 85% potassium hydroxide in 900 ml of 95% ethanol, and the resulting mixture heated to reflux. After about one-half hour, the reaction became quite vigorous. The mixture was stirred under relux overnight, cooled to room temperature, and made strongly acidic with concentrated hydrochloric acid. The mixture was cooled and filtered. The solid was taken up in diethyl ether, dried, and evaporated under vacuum to yield 2-methyl-2-tetradecylmalonic acid, mp 83°-85° C.

The solid was heated with stirring to 165° C., whereupon evolution of $CO_2$ began. The temperature rose rapidly to 190° C. with rapid evolution of $CO_2$. The solid was then heated for an additional ½ hour at 185°-190° C. to yield 81.3 g of 2-methylhexadecanoic acid, mp 44°-46° C.

Representative Example of the Preparation of an Amide

Preparation of (N-2,4,6-trimethoxyphenyl)-2-methylhexadecanamide

2-Methylhexadecanoic acid (27.0 g 0.1 mol) was mixed with 100 ml of thionyl chloride and the resulting mixture was stirred and heated under reflux for eight hours and then stirred at room temperature overnight. The mixture was concentrated under vacuum, diethyl ether was added and the mixture again concentrated under vacuum. The residue was distilled to yield 25.8 g of 2-methylhexadecanoyl chloride, bp 120°-125° C. at 0.25 mm Hg.

2,4,6-Trimethoxyphenylamine hydrochloride (6.58 g, 0.03 mol) and 8.3 ml (6.06 g, 0.06 mol) of triethylamine were dissolved in 100 ml of tetrahydrofuran. To this mixture was slowly added, with stirring, 8.65 g of 2-methylhexa-decanoyl chloride. The resulting mixture was stirred at room temperature overnight, filtered, and the filtrate concentrated under vacuum. Water was added to the residue, the resulting solid collected by filtration, and recrystallized from isopropyl ether to yield 12.0 g of N-2,4,6-trimethoxyphenyl)-2-methylhexadecanamide, mp 109°-111° C.

Employing the general methods detailed above, the following compounds in accordance with the present invention were prepared.

TABLE 3

| Example | Compound | M.p. (°C.) |
| --- | --- | --- |
| 1 | N—(2,6-dimethylphenyl)-2,2-dimethyldodecanamide | 53–54 |
| 2 | N—(2,6-diethylphenyl)-2,2-dimethyldodecanamide | 70–72 |
| 3 | N—[2,6-bis(1-methylethyl)phenyl]-2,2-dimethyldodecanamide | 119–120 |
| 4 | N—(2-ethoxy-6-methylphenyl)-2,2-dimethyldodecanamide | 60–62 |
| 5 | 2-methyl-N—[2,6-bis(1-methylethyl)phenyl]tetradecanamide | 94–96 |
| 6 | (Z)—N—(2,6-diethylphenyl)-2-methyl-9-octadecenamide | Wax |
| 7 | (Z)—N—(2,6-diethylphenyl)-2,2-dimethyl-9-octadecenamide | Wax |
| 8 | (Z)—N—(2-methoxy-6-methylphenyl)-2,2-dimethyl-11-eicosenamide | Wax |
| 9 | 2,2-dimethyl-N—(2,4,6-trimethoxyphenyl)dodecanamide | 59–60 |
| 10 | 2-methyl-N—(2,4,6-trimethoxyphenyl)teradecanamide | 109–111 |
| 11 | 2-ethyl-N—(2,4,6-trimethoxyphenyl)tetradecanamide | 98–99 |
| 12 | 2,2-dimethyl-N—(2,4,6-trimethoxyphenyl)tetradecanamide | 61–63 |
| 13 | 2-methyl-N—(2,4,6-trimethoxyphenyl)hexadecanamide | 109–111 |
| 14 | 2,2-dimethyl-N—(2,4,6-trimethoxyphenyl)hexadecanamide | 63–65 |
| 15 | 2,2-dimethyl-N—(2,4,6-trimethoxyphenyl)octadecanamide | 68–70 |
| 16 | 1-decyl-N—(2,4,6-trimethoxyphenyl)cyclobutanecarboxamide | 89–90 |
| 17 | 1-decyl-N—(2,4,6-trimethoxyphenyl)cyclopentanecarboxamide | 73–74 |
| 18 | (Z)—2-methyl-N—(2,4,6-trimethoxyphenyl)-9-octadecenamide | Wax |
| 19 | (Z)—2,2-dimethyl-N—(2,4,6-trimethoxyphenyl)-9-octadecenamide | Wax |
| 20 | (Z)—2,2-dimethyl-N—(2,4,6-trimethoxyphenyl)-11-eicosenamide | Wax |
| 21 | N—(4,6-dimethoxy-5-pyrimidinyl)-2,2-dimethyldodecanamide | 100–101 |
| 22 | N—(4,6-dimethoxy-2-phenyl-5-pyrimidinyl)-2,2-dimethyldodecanamide | 98–99 |
| 23 | N—(4,6-dimethoxy-5-pyrimidinyl)-2-methyltetradecanamide | 119–120 |
| 24 | N—(4,6-dimethoxy-5-pyrimidinyl)-2-ethyltetradecanamide | 115–116 |
| 25 | N—(4,6-dimethoxy-5-pyrimidinyl)-2,2-dimethyltetradecanamide | 93–94 |
| 26 | N—(4,6-diethoxy-5-pyrimidinyl)-2-methyltetradecanamide | 106–107 |
| 27 | 1-decyl-N—(4,6-dimethoxy-pyrimidin-5-yl)cyclopentanecarboxamide | 107–108 |
| 28 | (Z)—N—(4,6-dimethoxy-5-pyrimidinyl)-2,2-dimethyl-11-eicosenamide | Wax |
| 29 | 2-methyl-N—[1-(2-pyridinyl)ethyl]dodecanamide | 77–78 |
| 30 | 2-ethyl-N—[1-(2-pyridinyl)ethyl]dodecanamide | 72–74 |
| 31 | 2-propyl-N—[1-(2-pyridinyl)ethyl]dodecanamide | 76–78 |
| 32 | α-decyl-N—[1-(2-pyridinyl)ethyl]benzenepropanamide | 68–70 |
| 33 | 2-methyl-N—[1-(2-pyridinyl)ethyl]tetradecanamide | 68–71 |
| 34 | 2-ethyl-N—[1-(2-pyridinyl)ethyl]tetradecanamide | 84–85 |
| 34 | 2-methyl-N—[1-(2-pyridinyl)ethyl]hexadecanamide | 88–89 |
| 35 | 2,2-dimethyl-N—[1-(2-pyridinyl)ethyl]hexadecanamide | 32–33 |

We claim:
1. A compound having the formula

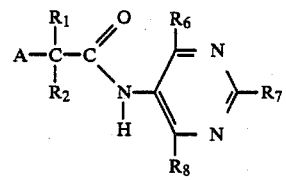

wherein
A is an unbranched hydrocarbon group having from one to twenty carbon atoms and which may optionally have from one to three carbon-carbon double bonds;
$R_1$ is hydrogen, alkyl of from one to four carbon atoms or phenylmethyl:
$R_2$ is alkyl of from one to four carbon atoms or phenylmethyl; or $R_1$ and $R_2$ when taken together with the carbon atom to which they are attached form a saturated carbocyclic ring of from three to seven carbon atoms;

$R_6$ is alkoxy of from one to four carbon atoms; and $R_7$ and $R_8$ are independently hydrogen or alkoxy of from one to four carbon atoms.

2. A compound in accordance with claim 1 selected from the group consisting of

N-(4,6-dimethoxy-5-pyrimidinyl)-2,2-dimethyldodecanamide;

N-(4,6-dimethoxy-2-phenyl-5-pyrimidinyl)-2,2-dimethyldodecanamide;

N-(4,6-dimethoxy-5-pyrimidinyl)-2-methyltetradecanamide;

N-(4,6-dimethoxy-5-pyrimidinyl)-2-ethyltetradecanamide;

N-(4,6-dimethoxy-5-pyrimidinyl)-2,2-dimethyltetradecanamide;

N-(4,6-diethoxy-5-pyrimidinyl)-2-methyltetradecanamide;

1-decyl-N-(4,6-dimethoxypyrimidin-5-yl)cyclopentanecarboxamide; and (Z)-N-(4,6-dimethoxy-5-pyrimidinyl)-2,2-dimethyl-11-eicosenamide.

3. A pharmaceutical composition useful for inhibiting the intestinal absorption of cholesterol comprising an ACAT-inhibitory effective amount of a compound as defined by claim 1 in combination with a pharmaceutically acceptable carrier.

4. A method of inhibiting intestinal absorption of cholesterol comprising administering to a patient an ACAT-inhibitory effective amount of a compound as defined by claim 1.

* * * * *